US010064577B1

(12) United States Patent
Goldberg

(10) Patent No.: US 10,064,577 B1
(45) Date of Patent: Sep. 4, 2018

(54) MULTI-LEVEL PINCH DYNAMOMETER OR GAUGE, A KIT OF COMPONENTS, AND METHODS OF MAKING AND USING SAME

(71) Applicant: Elliott Goldberg, Scarsdale, NY (US)

(72) Inventor: Elliott Goldberg, Scarsdale, NY (US)

( * ) Notice: Subject to any disclaimer, the term of this patent is extended or adjusted under 35 U.S.C. 154(b) by 69 days.

(21) Appl. No.: 14/714,815

(22) Filed: May 18, 2015

Related U.S. Application Data

(60) Provisional application No. 62/004,817, filed on May 29, 2014.

(51) Int. Cl.
*A61B 5/22* (2006.01)
*G01L 5/00* (2006.01)
*A61B 5/00* (2006.01)
*A61B 19/02* (2006.01)

(52) U.S. Cl.
CPC .............. *A61B 5/225* (2013.01); *A61B 5/742* (2013.01); *A61B 19/0264* (2013.01); *G01L 5/00* (2013.01); *A61B 2019/0265* (2013.01)

(58) Field of Classification Search
CPC ....... A61B 5/225; A61B 5/742; A61B 5/1107; A61B 5/1125; G01L 5/00
See application file for complete search history.

(56) References Cited

U.S. PATENT DOCUMENTS

| 4,553,746 A * | 11/1985 | Lee ........................ A63B 21/05 482/49 |
| 2003/0093012 A1* | 5/2003 | Smyser .................. A61B 5/225 600/595 |
| 2004/0107592 A1* | 6/2004 | Mattis .................. A61B 5/1071 33/512 |

* cited by examiner

*Primary Examiner* — Erika J Villaluna
(74) *Attorney, Agent, or Firm* — Weiner & Burt, P.C.; Irving M. Weiner; Pamela S. Burt

(57) ABSTRACT

A multi-level pinch dynamometer or gauge which measures pinch strength. A 5-position mechanism provides quick insert and removal of a bottom pinch plate from a multi-position rack. The digital model gauge head displays strength readings, calculated results, and user demographics.

1 Claim, 11 Drawing Sheets

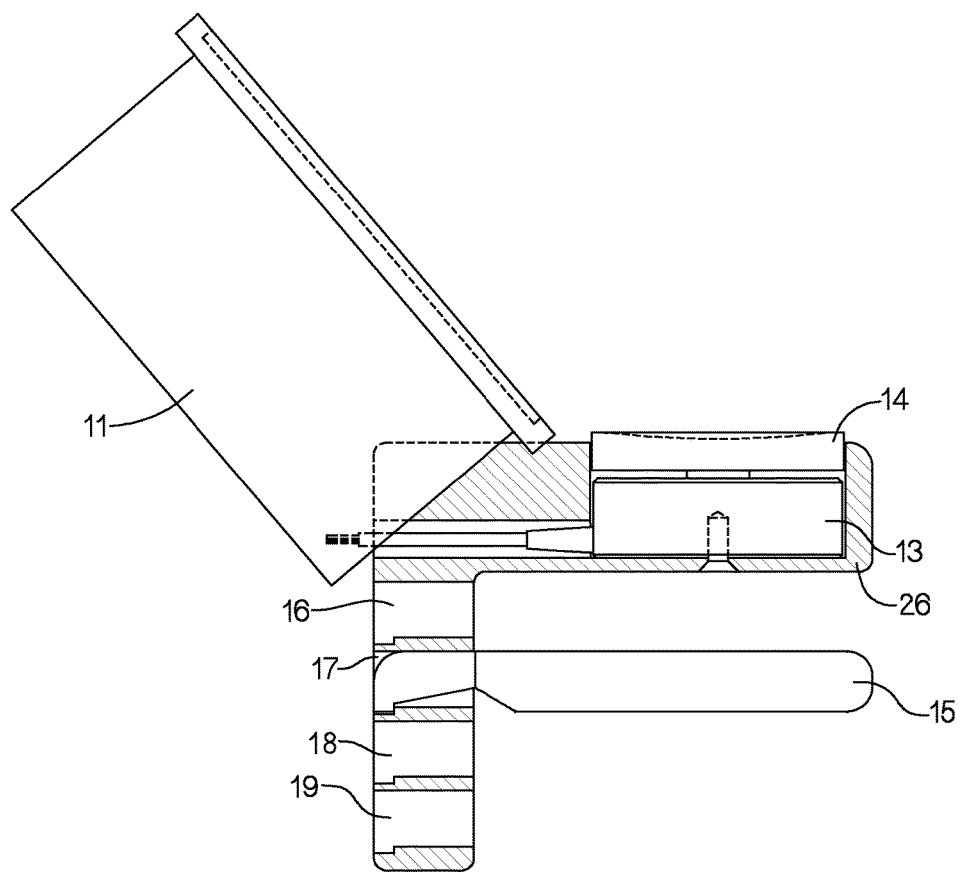
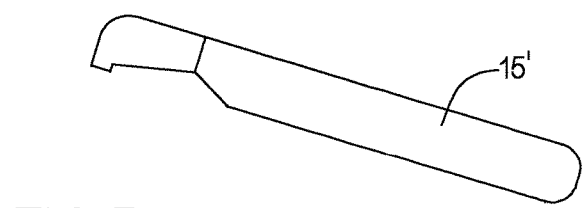
FIG 5

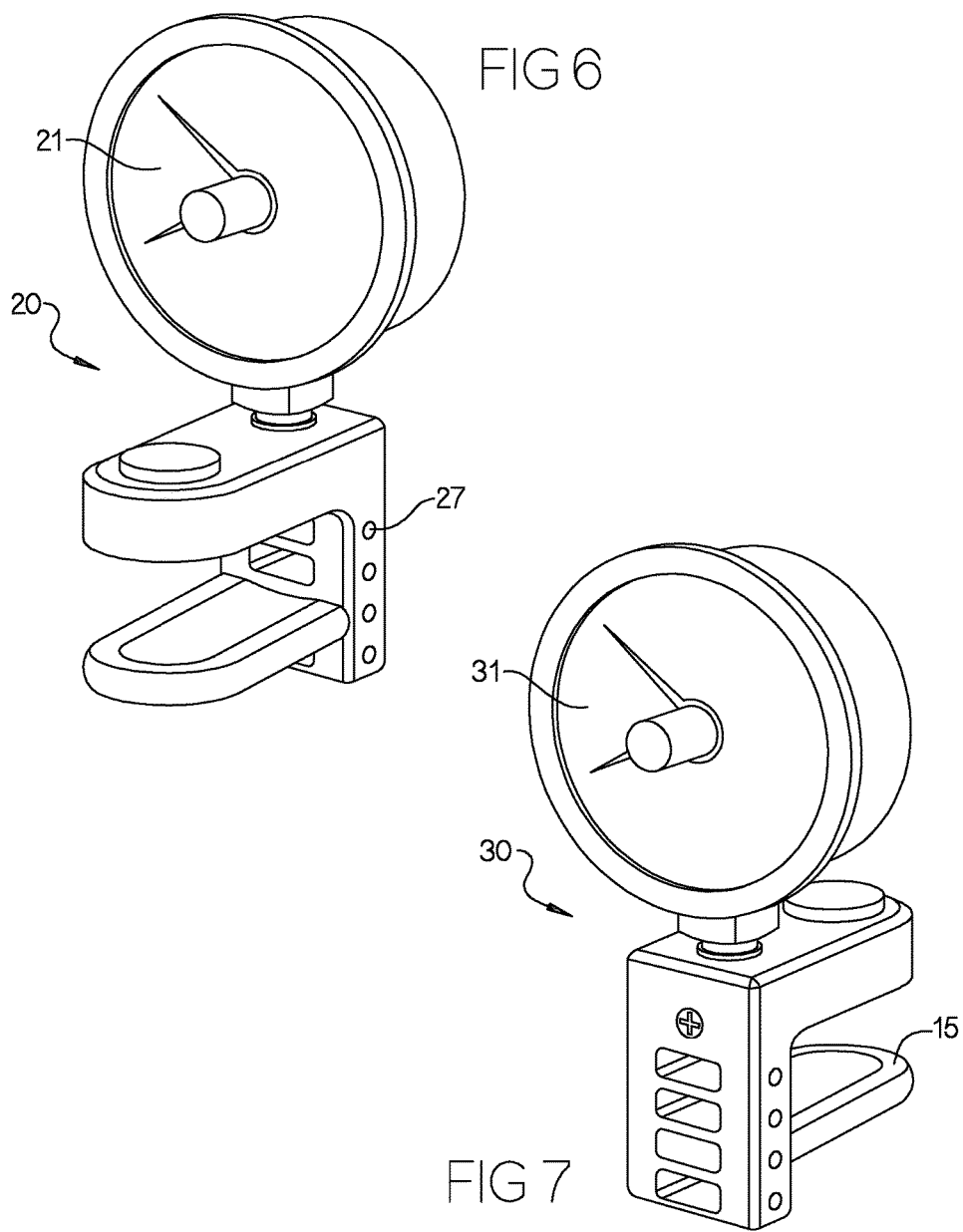

MULTI-LEVEL PINCH DYNAMOMETER OR GAUGE, A KIT OF COMPONENTS, AND METHODS OF MAKING AND USING SAME

CROSS-REFERENCE TO RELATED APPLICATION

The present application is a continuation-in-part of and claims priority from U.S. Provisional Patent Application Ser. No. 62/004,817 filed May 29, 2014.

BACKGROUND OF THE INVENTION

The present invention relates generally to a multi-level pinch dynamometer or gauge, a kit of components, and methods of making and using same.

More particularly, the present invention relates to a multi-level pinch dynamometer or gauge which accommodates all hand sizes and allows for a variety of test procedures and protocols, a kit of components, and methods of making and using same.

It is a desideratum of the present invention to avoid the animadversions of conventional pinch dynamometers, and to provide an easy-to-use multi-level pinch dynamometer or gauge, a kit of components, and methods of making and using same.

BRIEF SUMMARY OF THE INVENTION

The term "subject" as used herein means the person being tested using the multi-level pinch dynamometer apparatus disclosed herein.

The term "practitioner" as used herein means the person testing the subject using the multi-level pinch dynamometer apparatus disclosed herein.

The present invention provides multi-level pinch dynamometer apparatus which measures pinch strength, comprising: a multi-position pinch grip device; a gauge head; transmission mean operably connected to the grip device and the gauge head for transmitting pressure or force generated by a subject from the grip device to the gauge head; the gauge head displays readings indicative of the pressure or force; the grip device includes a fixed stationary first mechanism and a multi-position mechanism for quick insertion and removal therefrom of a second mechanism; and the pressure or force is generated by the subject pinching the first mechanism, or by pinching together the first and second mechanisms; and methods of making and using the apparatus.

The present invention also provides a kit of components, comprising: a carrying case; the carrying case including therein a multi-level pinch dynamometer apparatus which measures pinch strength, comprising: a multi-position pinch grip device; a gauge head; transmission mean operably connected to the grip device and the gauge head for transmitting pressure or force generated by a subject from the grip device to the gauge head; the gauge head displays readings indicative of the pressure or force; the grip device includes a fixed stationary first mechanism and a multi-position mechanism for quick insertion and removal therefrom of a second mechanism; and the pressure or force is generated by the subject pinching the first mechanism, or by pinching together the first and second mechanisms; the carrying case further including therein a hand dynamometer; and the carrying case further including therein a range-of-motion finger-goniometer; and methods of making and using the kit of components.

An object of present invention is to provide a multi-level pinch dynamometer or gauge which accommodates all hand sizes, and methods of making and using same.

Another object is to provide such a multi-level pinch dynamometer apparatus wherein the grip device includes a multi-position rack for selectively and releasably holding the second mechanism in a selected position.

Another object of the present invention is to provide an apparatus as described herein which measures pinch strength.

Another object of the present invention is to provide such a multi-level pinch dynamometer apparatus wherein the gauge head faces the subject.

Another object of the present invention is to provide an apparatus as described hereinabove having a multi-level design that can be used to perform more tests than conventional single-level pinch dynamometers.

Another object is to provide such a multi-level pinch dynamometer apparatus wherein the gauge head faces away from the subject.

Another object of the present invention is to provide an apparatus as described hereinabove which includes a hydraulic or electronic gauge head that displays strength readings, calculated results, and user demographics.

Another object is to provide such a multi-level pinch dynamometer apparatus wherein: the multi-position mechanism comprises a rack which is disposed substantially perpendicular to the fixed stationary first mechanism; and the rack includes a plurality of apertures therein each of which is designed and dimensioned to temporarily retain therein the second mechanism.

Another object of the present invention is to provide an apparatus as described hereinabove which includes a gauge head that contains a mechanism which coverts raw pressure, force, or electronic signals into useable data points.

Another object of the present invention is to provide an apparatus as described hereinabove which includes a force or pressure transducer or sensor to initiate and transmit force or pressure to a gauge.

Another object of the present invention is to provide an apparatus as described hereinabove which includes a transducer that may be a load cell or pressure sensor (electronic) or a bellows (hydraulic), or a spring or other resilient material Another object of the present invention is to provide an apparatus as described hereinabove which includes a multi-level rack to accommodate a bottom pinch pad.

Other objects, advantages, features and modifications of the present invention will become more apparent to those persons skilled in this particular area of technology and to other persons after having been exposed to the present patent specification with its accompanying drawings.

BRIEF DESCRIPTION OF THE SEVERAL VIEWS OF THE DRAWINGS

FIG. 5 shows a sectional view taken along the line 5-5 of FIG. 2.

FIG. 6 is a perspective view of a second embodiment.

FIG. 7 is a perspective view of a third embodiment.

DETAILED DESCRIPTION OF THE INVENTION

Figure 1:
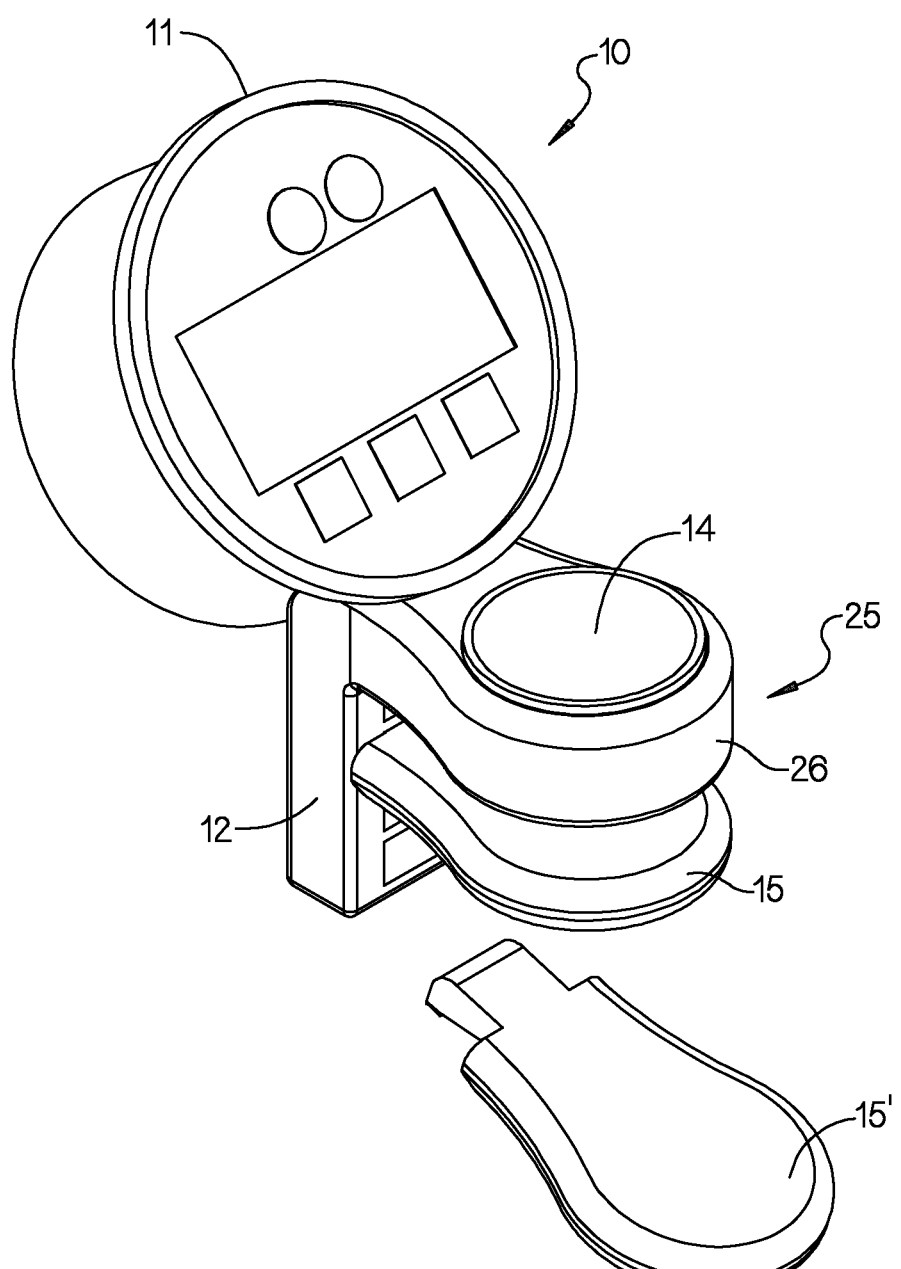
FIG. 1 shows a perspective view of an apparatus according to a first embodiment of the invention.
Figure 2:
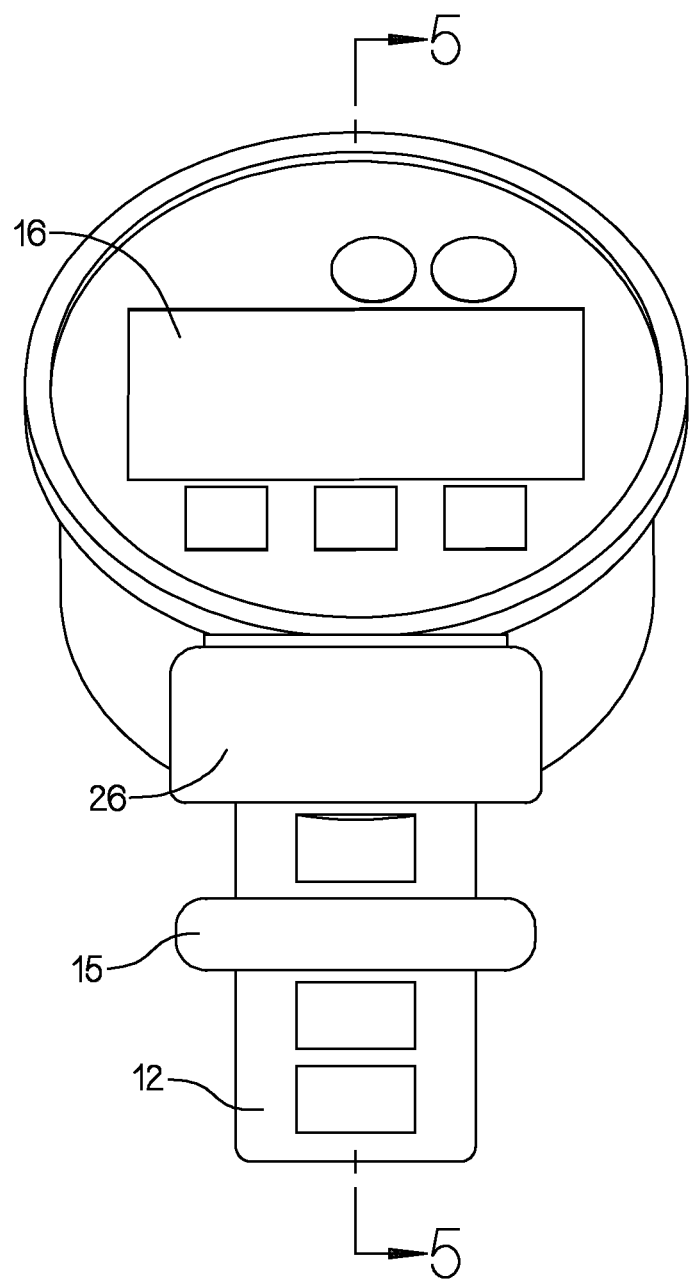
FIG. 2 shows a front elevational view of the FIG. 1 apparatus.

Like components are designated by like reference numbers

With reference to the drawings, there is shown a digital model of multi-level pinch dynamometer or gauge apparatus 10 according to first embodiment of the invention.

The apparatus 10 includes a gauge head 11, a 5-position multi-level rack 12, an internal transducer 13, a stationary mechanism 25 (including an upper plate 26 with a pinch pad 14), a bottom pinch pad or plate 15, and a digital display 16.

Figure 3:
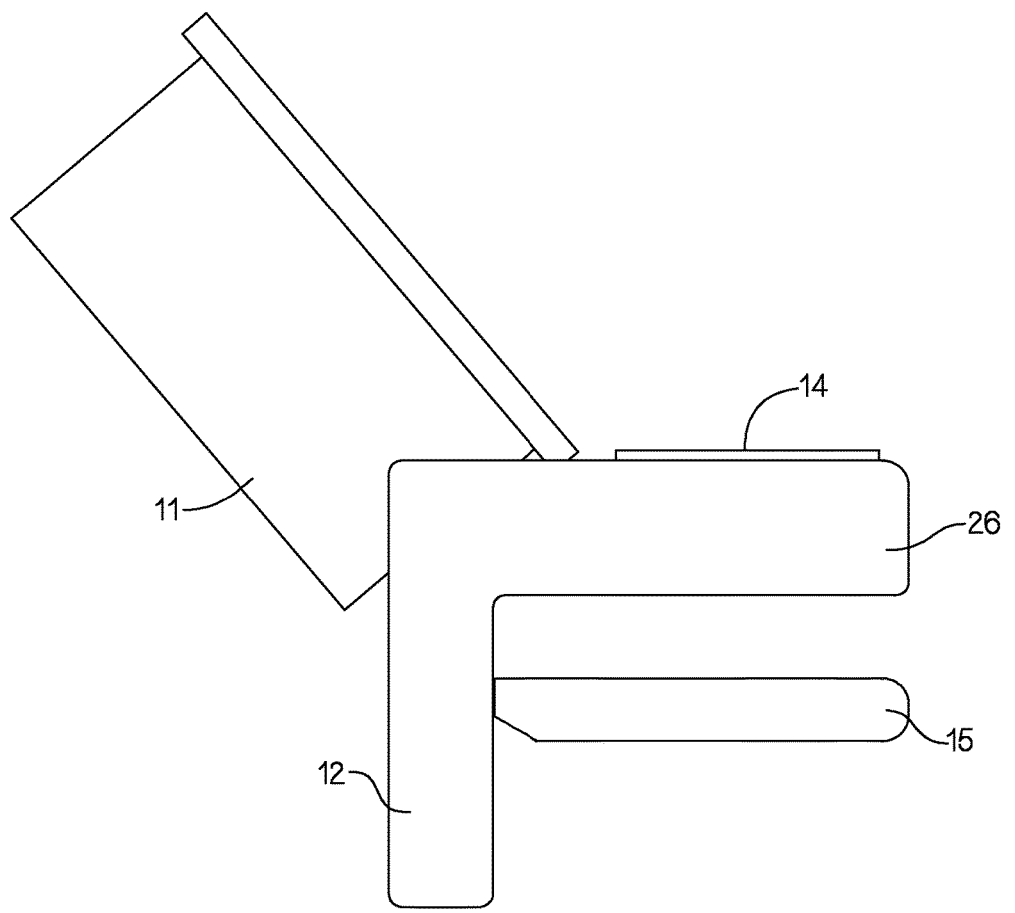
FIG. 3 shows left side elevational view of the FIG. 1 apparatus.
Figure 4:
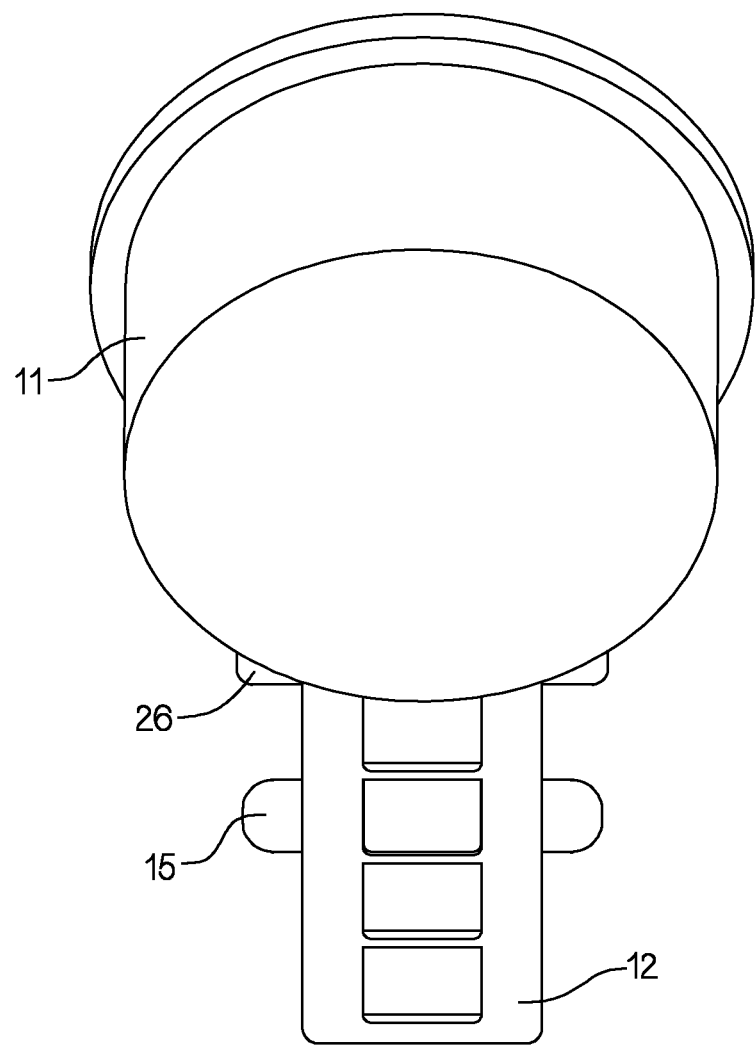
FIG. 4 shows a rear elevational view of the FIG. 1 apparatus

FIGS. 1, 3 and 5 include an extra bottom plate 15' to clearly depict its configuration.

The apparatus 10 is used to measure pinch strength, and constitutes a 5-position pinch grip gauge.

The five positions are one stationary or fixed, and four variable.

The gauge head 11 may be either hydraulic or electronic.

The gauge head 11 displays strength readings, calculated results, and user demographics on the display 16.

The gauge head 11 contains a mechanism (not shown) for converting raw pressure, force, or electronic signals into useable data points.

The transducer 13 is a force or pressure transducer to initiate and transmit force or pressure to the gauge head 11.

The transducer may be a load or pressure cell 13 (electronic) or a bellows (hydraulic).

The multi-level rack 12 is used for accommodating the bottom pinch plate 15.

The multi-level rack 12 comprises a four-position rack.

In FIGS. 1, 3 and 5, the bottom pinch plate 15 is shown in two positions (unattached to the rack 12 and also mounted in the rack 12) merely for illustrative purposes only.

The multi-level pinch dynamometer apparatus 10 measures pinch strength, comprising: the multi-position pinch grip device; a gauge head 11; transmission means 13 operably connected to the grip device and the gauge head 11 for transmitting pressure or force from the grip device to the gauge head 11; the gauge head 11 displays readings indicative of the pressure or force; the grip device includes a fixed stationary first mechanism 25 and a multi-position mechanism for quick insertion and removal therefrom of a second mechanism 15; and the first and second mechanisms 25 and 15 being pinched together by a subject to generate the pressure or force; and methods of making using the apparatus 10.

The multi-position mechanism comprises the rack which is disposed substantially perpendicular to the fixed stationary first mechanism 14; and the rack 12 includes a plurality of apertures 16, 17, 18 and 19 therein each of which is designed and dimensioned to temporarily retain therein the second mechanism 15.

FIG. 6 is a perspective view of a second embodiment of a feedback model apparatus 20 where the gauge 21 faces toward the subject to enhance compliance and feedback.

Spring plunger devices 27 in the rack 12 enable the easy-to-use, attach/detach features for the bottom paddle 15.

Alternatively, the spring plunger devices 27 can be on or part of the paddle 15.

FIG. 7 is a perspective view of a third embodiment in the form of a clinical model apparatus 30 where the gauge 31 faces away from the subject (toward the practitioner to block readings from the subject.

Figure 8:
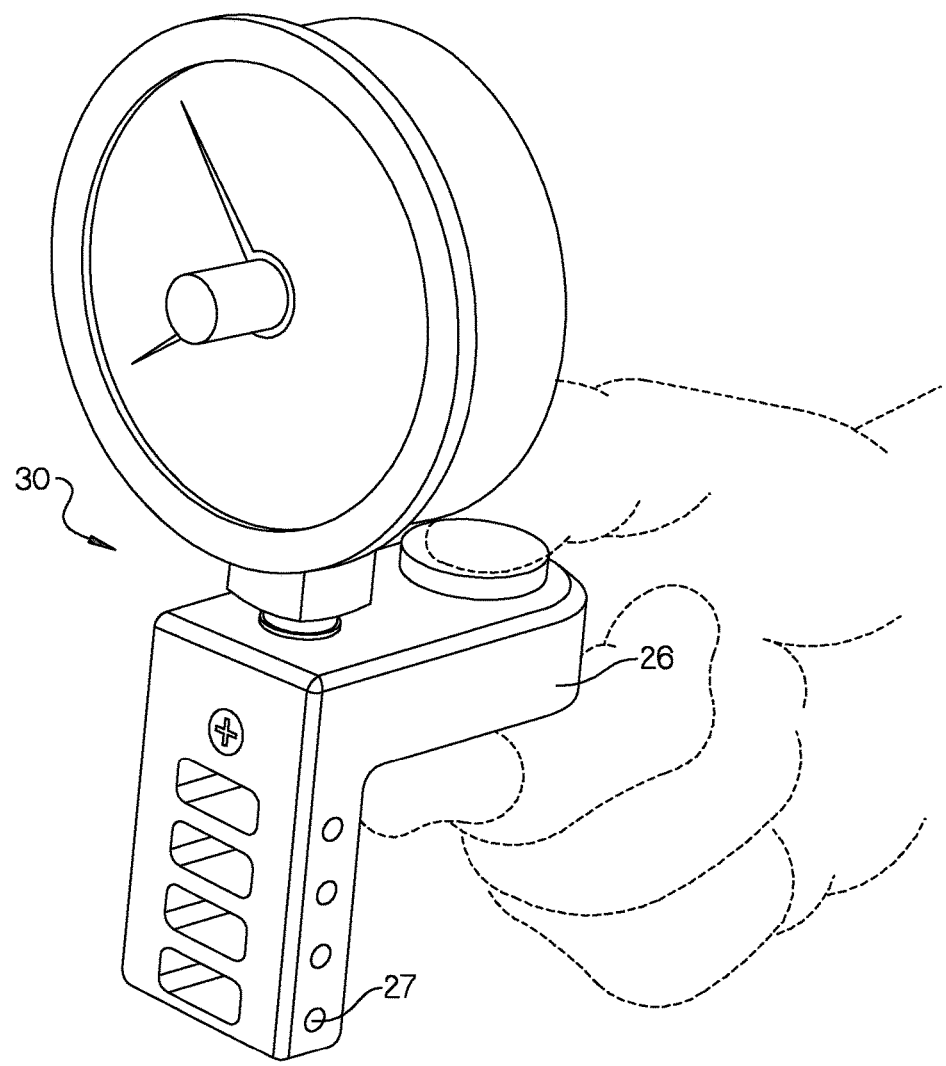
FIG. 8 is a perspective view of the third embodiment in use without the bottom paddle.

FIG. 8 is a perspective view of the third embodiment in the form of in use without the bottom pinch pad or plate or paddle 15 to accommodate small hands (same pinch width as current conventional pinch gauges).

Figure 9:
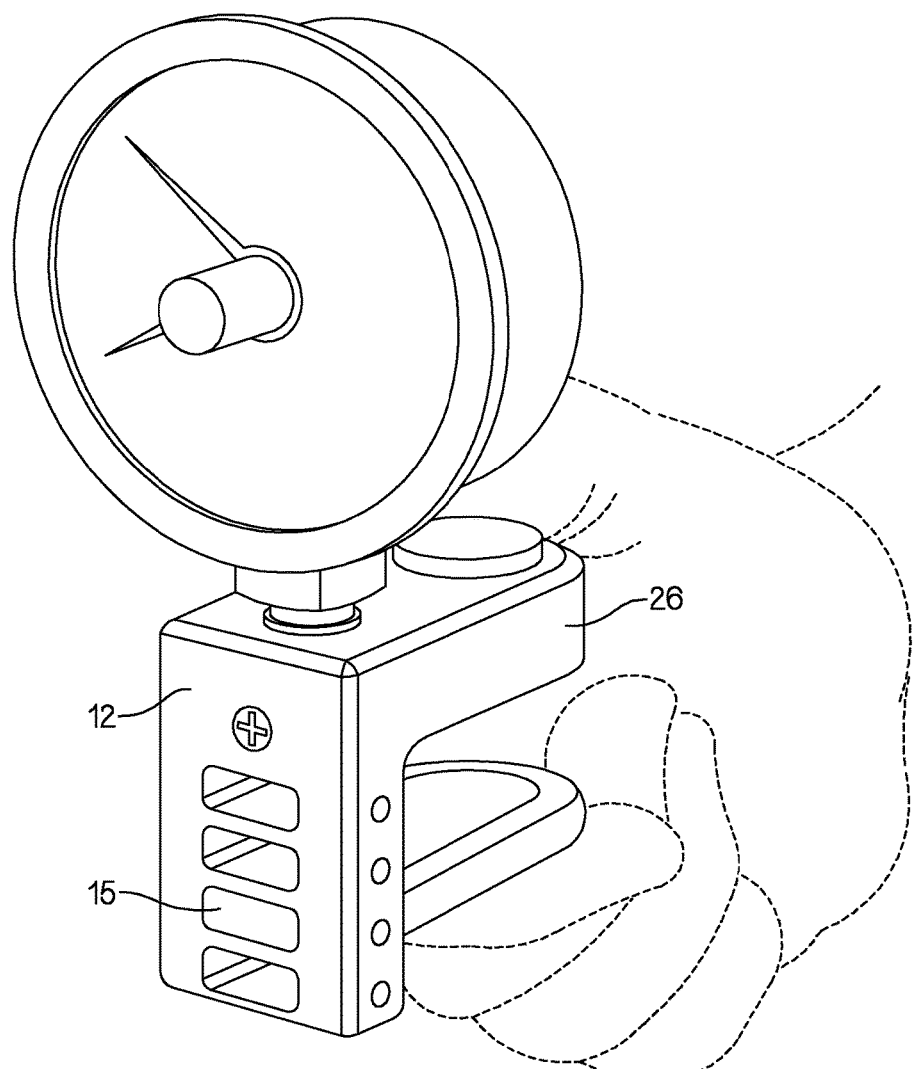
FIG. 9 is a perspective view of the third embodiment in use with the bottom paddle.

FIG. 9 is a perspective view of the third embodiment in use with the paddle 15 in the multi-level rack 12 to accommodate large hands.

Figure 10:
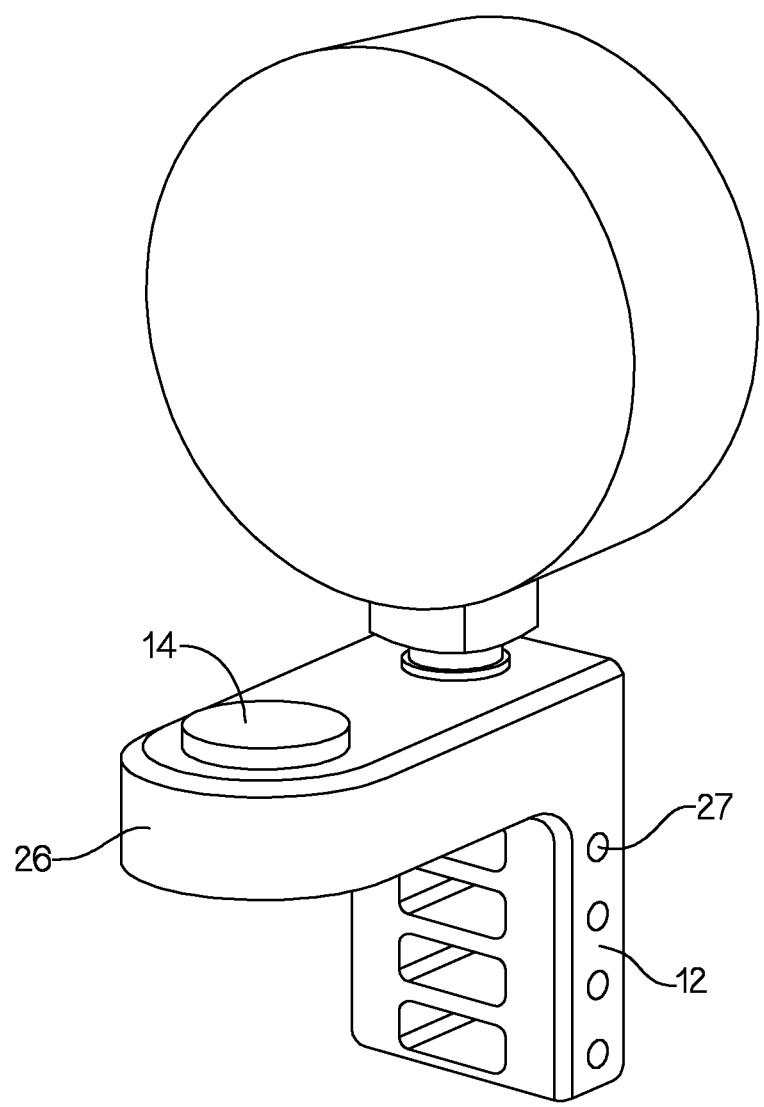
FIG. 10 is a rear view of the FIG. 8 apparatus.

FIG. 10 illustrates the rear view of the FIG. 8 apparatus 30.

Figure 11:
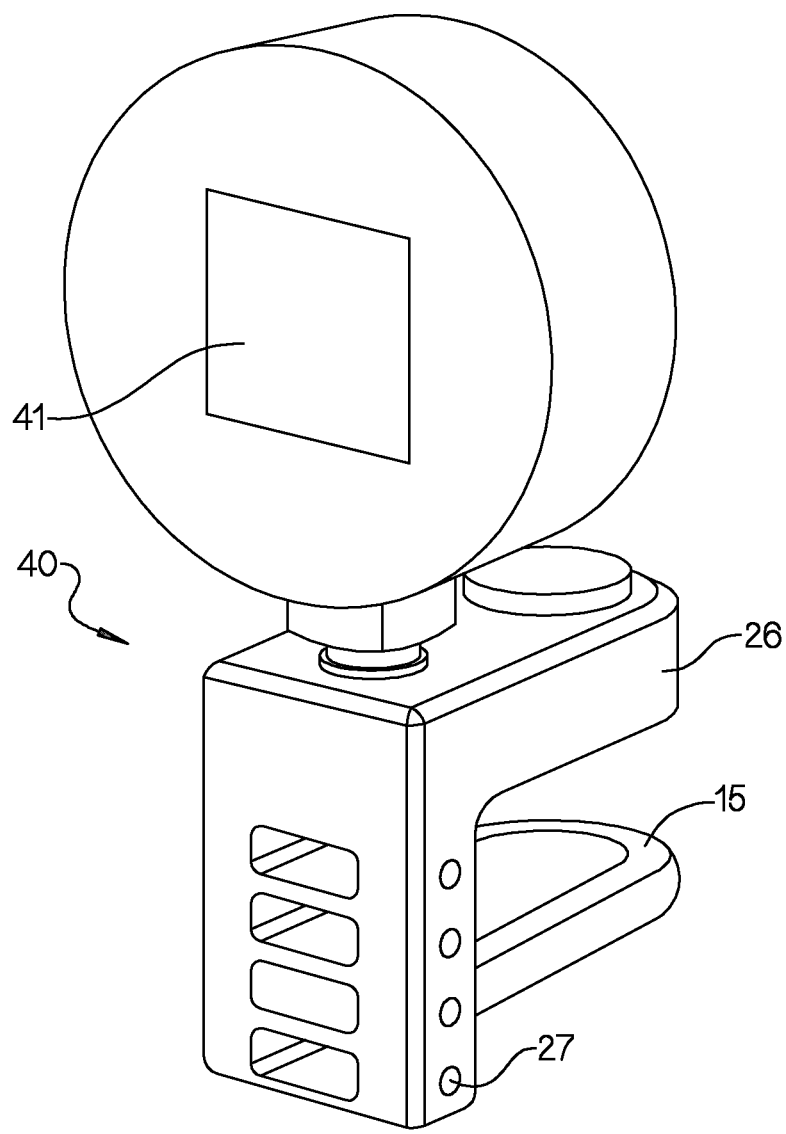
FIG. 11 shows a fourth embodiment.

FIG. 11 shows a fourth embodiment in the form of an electronic clinical model apparatus 40 where the gauge display 41 faces toward the practitioner.

Figure 12:
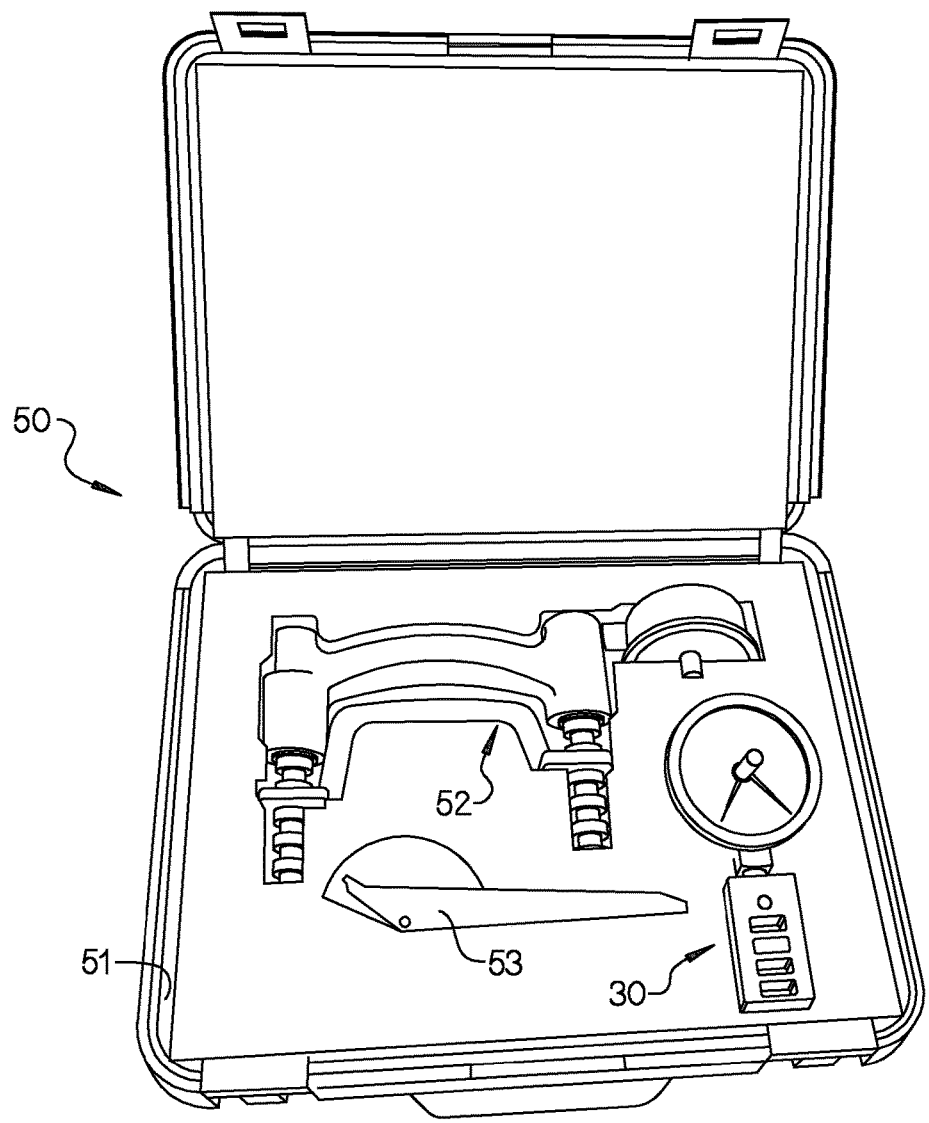
FIG. 12 shows a kit of components according to the present invention.

FIG. 12 shows a kit of components 50 having a carrying case 51, the clinical model of the 5-position grip gauge apparatus 30, a hand dynamometer 52, and a range-of-motion finger-goniometer 53.

The multi-level design accommodates all hand sizes.

Furthermore, the multi-level design is used for performing more tests and protocols than single-level pinch dynamometers conventionally in use.

Also, the apparatus 10, 20 or 30 is used to prevent spurious readings which may be intended by the person being tested.

The invention covers clinical (gauge facing away from the subject) models. and feedback (gauge facing toward the subject) models.

The invention also covers hydraulic models with a bellows mechanism (and any other mechanism including a spring) to transmit pressure (force) to the gauge.

The invention also covers digital models with a load cell or pressure sensor mechanism (and any other mechanism) to transmit pressure (force) to the gauge.

The invention also covers a 5-position mechanism using numerous methods of quick insert and removal of the paddle from the rack.

The invention not only covers a 5 position apparatus (1 stationary and 4 variable) as well as other configurations (1 stationary, and 1, 2, etc. variable).

The digital model gauge head displays strength readings, calculated results, and user demographics.

The digital model gauge has a series of up/down and left/right arrows which can be used by the practitioner to enter and retrieve data/information from memory to the gauge screen or through Bluetooth/wireless/or wired connection to a computer.

While the foregoing describes only exemplary embodiments of the present invention, it is to be understood that the present invention covers all variations, modifications and changes thereof which will occur to those persons skilled in the art and to other persons after having been exposed to the present patent application.

The invention claimed is:

1. A multi-level pinch dynamometer apparatus for obtaining a measurement of pinch strength of a subject user, comprising:
   a pinch grip device;
   a gauge head including a display;
   transmission means operably connected to said pinch grip device and said gauge head for transmitting a pressure or force electronic signal generated by a subject user from said pinch grip device to said gauge head;

said pinch grip device includes a first mechanism which remains in a fixed or stationary position relative to said gauge head, and a second mechanism which is movable among four variable positions for quick insertion therein and removal therefrom any one of four apertures in a multi-level rack;

said multi-level rack is disposed substantially perpendicular to said first mechanism;

said multi-level rack includes said four apertures therein, each aperture of which is designed and dimensioned to temporarily retain therein said second mechanism;

said transmission means includes an internal transducer;

said internal transducer initiates and transmits the electronic signal to said gauge head;

said gauge head displays readings giving a measurement of the pressure or force generated by the subject user;

the multi-level pinch dynamometer apparatus being useable with and without said second mechanism to accommodate hands of the subject user;

the pressure force may be generated by the subject user pinching the first mechanism only, and may also be generated by pinching together the first and second mechanisms said gauge head faces toward or away from the subject user;

spring plunger devices disposed on said multi-level rack or on said second mechanism and comprising attach/detach means for said second mechanism;

said fixed stationary first mechanism includes an upper plate with a pinch pad;

said second mechanism comprises a bottom pinch pad, plate or paddle; and said gauge head displays on said display pinch strength readings of the subject user.

\* \* \* \* \*